US011369773B2

(12) United States Patent
Donahue et al.

(10) Patent No.: US 11,369,773 B2
(45) Date of Patent: Jun. 28, 2022

(54) TARGETED CARDIAC THERAPY

(71) Applicant: RITHIM BIOLOGICS, INC., Woodbine, MD (US)

(72) Inventors: John Kevin Donahue, Holliston, MA (US); Ronald Lee Anderson, Woodbine, MD (US)

(73) Assignee: RITHIM BIOLOGICS, INC., Woodbine, MD (US)

( * ) Notice: Subject to any disclaimer, the term of this patent is extended or adjusted under 35 U.S.C. 154(b) by 186 days.

(21) Appl. No.: 16/477,169

(22) PCT Filed: Jan. 11, 2018

(86) PCT No.: PCT/US2018/013408
§ 371 (c)(1),
(2) Date: Jul. 10, 2019

(87) PCT Pub. No.: WO2018/132620
PCT Pub. Date: Jul. 19, 2018

(65) Prior Publication Data
US 2019/0351184 A1    Nov. 21, 2019

Related U.S. Application Data

(60) Provisional application No. 62/445,604, filed on Jan. 12, 2017.

(51) Int. Cl.
*A61M 25/00* (2006.01)
*A61B 90/00* (2016.01)
*A61M 1/00* (2006.01)
*A61B 34/20* (2016.01)

(52) U.S. Cl.
CPC ....... *A61M 25/0068* (2013.01); *A61B 90/361* (2016.02); *A61M 1/0058* (2013.01); *A61M 25/0082* (2013.01); *A61B 34/20* (2016.02); *A61B 2090/3966* (2016.02)

(58) Field of Classification Search
CPC .......... A61M 25/0068; A61M 25/0082; A61B 18/00; A61B 2018/00005; A61B 18/14
See application file for complete search history.

(56) References Cited

U.S. PATENT DOCUMENTS

| | | | |
|---|---|---|---|
| 4,946,440 A * | 8/1990 | Hall | A61M 16/0833 604/164.09 |
| 6,217,576 B1 | 4/2001 | Tu et al. | |
| 6,309,370 B1 | 10/2001 | Haim et al. | |
| 7,764,994 B2 | 7/2010 | Fuimaono et al. | |
| 2006/0229594 A1 * | 10/2006 | Francischelli | A61B 34/20 606/27 |

OTHER PUBLICATIONS

International Search issued in WO 2018/132620 A1, filed Jul. 19, 2018, which claims priority from PCT/US2018/013408, filed Jan. 11, 2018.

* cited by examiner

*Primary Examiner* — Deanna K Hall
(74) *Attorney, Agent, or Firm* — Wiley Rein LLP

(57) ABSTRACT

The present invention relates to a targeted cardiac therapy device that can precisely deliver therapeutic compounds to desired locations on, around or within the heart of a patient, and methods of treating conduction system disease, sinus node dysfunction, atrial fibrillation, myocardial infarction, and heart failure, using the described devices to deliver genetically engineered vectors or cells, proteins, stem cells, small molecule pharmaceuticals and biologics.

9 Claims, 2 Drawing Sheets

TARGETED CARDIAC THERAPY

CROSS REFERENCE

This Application is a § 371 National Stage Application of PCT/US2018/013408, filed Jan. 11, 2018, which claims priority benefit of U.S. Provisional Application No. 62/445,604, filed Jan. 12, 2017, the contents of which are hereby incorporated by reference in their entireties.

STATEMENT REGARDING FEDERALLY SPONSORED RESEARCH OR DEVELOPMENT

The research leading to the present invention was supported, in part by the National Center For Advancing Translational Sciences of the National Institutes of Health under Award Number R41TR002425.

TECHNICAL FIELD

The present disclosure relates to devices for the targeted cardiac delivery of therapeutic compounds and the uses thereof. More particularly, the embodiments described herein provide devices capable of delivering a therapeutic compound on, around or within a patient's heart. Specific embodiments provide methods of treating conduction system disease, sinus node dysfunction, atrial fibrillation, myocardial infarction, and heart failure, using the described devices to deliver genetically engineered vectors or cells, proteins, stem cells, small molecule pharmaceuticals and biologics.

BACKGROUND

Cardiac diseases are the most common causes of morbidity and mortality in the developed world. Coronary artery disease causing angina and myocardial infarction, cardiac arrhythmias causing stroke, syncope and sudden death, and heart failure causing disability and death are examples of cardiac diseases that greatly affect the lives of the afflicted as well as their families, employers and friends.

Limitations to prevention and therapy of cardiac diseases include the inability to directly target underlying disease mechanism for many of these diseases, and the limitations of off-target effects of systemically administered drugs that might otherwise be effective for other diseases. Potential clinical approaches to these limitations have included pharmacotherapy, gene therapy, cell therapy, protein and other biological therapies. To enhance efficacy and to limit off-target effects, it is desirable for these potential therapies to be delivered locally to the target portion(s) of the heart. In particular, there is a need for a device that can deliver therapeutic compounds, such as genetically engineered vectors or cells, proteins, stem cells, small molecule pharmaceuticals and biologics, precisely to a target on, around or within a patient's heart.

SUMMARY OF INVENTION

The disclosed embodiments include a device that comprises a catheter, wherein the catheter comprises a handle portion, a shaft portion, and a tip portion; a steering element configured to guide the catheter inside a patient's body; an internal conduit running along the longitudinal axis of the catheter; a fluid pathway disposed within the conduit; and a temperature control element configured to regulate the temperature of a fluid within the fluid pathway; wherein the tip portion comprises an actuator configured to operably connect the fluid pathway to the exterior of the catheter.

One embodiment of the device further comprises a sensor or marker configured to allow an operator to determine the location of the catheter within a patient's body. Another embodiment of the device further comprises a sensor configured to capture and transmit video, electrical or hemodynamic data, or images to a display. Yet another embodiment of the device further comprises an aspiration pathway disposed within the internal conduit configured to apply suction force from the tip portion to an exterior object.

The disclosed embodiments also include a method of treating a cardiac disease comprising delivering a therapeutic compound to a patient's heart using any one of the devices described herein. An embodiment involves a therapeutic compound selected from the group consisting of genetically engineered vectors or cells, proteins, stem cells, small molecule pharmaceuticals and biologics. The disclosed methods of treatment also pertain to cardiac diseases like conduction system disease, sinus node dysfunction, atrial fibrillation, myocardial infarction, and heart failure.

DETAILED DESCRIPTION

Figure 1A:
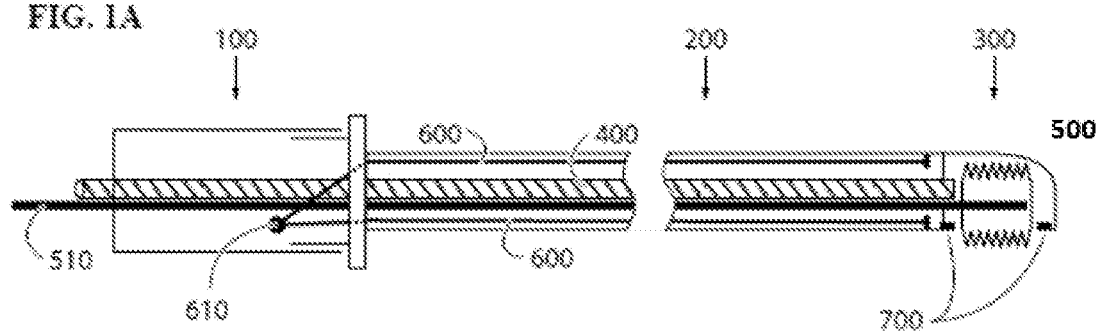
FIG. 1A is a transverse view of an embodiment of the device.

All patents and other publications identified are incorporated herein by reference for the purpose of describing and disclosing, for example, the methodologies described in such publications that might be used in connection with the present invention, but are not to provide definitions of terms inconsistent with those presented herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on information available to the applicants and do not constitute any admission as to the correctness of the dates or contents of these documents.

As used herein and in the claims, the singular forms "a," "an," and "the" include the plural reference unless the context clearly indicates otherwise. Throughout this specification, unless otherwise indicated, "comprise," "comprises" and "comprising" are used inclusively rather than exclusively, so that a stated integer or group of integers may include one or more other non-stated integers or groups of integers. The term "or" is inclusive unless modified, for example, by "either." Other than in the operating examples, or where expressly stated or otherwise indicated, all numbers expressing quantities of ingredients or reaction conditions used herein should be understood as modified in all instances by the term "about."

Unless defined otherwise, all technical and scientific terms used herein have the same meaning as those commonly understood to one of ordinary skill in the art. The terminology used herein is for the purpose of describing particular embodiments only, and is not intended to limit the scope of the present invention, which is defined solely by the claims. The terms male and female may be used interchangeably to describe corresponding components or complementary aspects thereof and are not a limitation to either particular structure unless context clearly indicates otherwise.

Headings are provided for convenience only and are not to be construed to limit the invention in any way. Unless defined otherwise, all technical and scientific terms used herein have the same meaning as those commonly understood to one of ordinary skill in the art. The terminology used herein is for the purpose of describing particular embodiments only, and is not intended to limit the scope of the present invention, which is defined solely by the claims. In order that the present disclosure can be more readily understood, certain terms are first defined. Additional definitions are set forth throughout the detailed description.

The disclosed embodiments include a catheter system that can be inserted endovascularly to target the endocardial surface of the heart. Alternatively, the catheter system can be inserted percutaneously into the pericardium to target the epicardial surface of the heart. The system may involve a single catheter, a catheter within a catheter, or a catheter with a sheath design. In certain embodiments, once inserted, the catheter can be maneuvered via its steering mechanism, via the steering mechanism of the sheath or outer catheter, or via manipulation of fixed curves in the inner catheter and/or sheath, and/or manipulation of the catheter shaft or handle to deliver the desired therapeutic material(s) to the whole heart, to the whole of individual chambers of the heart (left atrium, right atrium, left ventricle, right ventricle), or to specific areas within the chambers (including but not limited to the coronary arteries, a single coronary artery or portion thereof, the sinus node, the right ventricular outflow track, a myocardial infarction scar or the border zone around a myocardial infarction scar, and/or the components of the cardiac or autonomic nervous system). The catheter could target a single area or multiple areas or the whole heart. Delivered therapeutics could include individually or in combination small molecules, cells, gene(s), gene transfer vectors (including but not limited to viral vectors, non-viral vectors, and manufactured particles), proteins, lipids, carbohydrates, antibodies, or polymers, or any therapeutic substance or solution. The therapeutic could be delivered as a liquid if it exists in that state, or it could be delivered in a solution composed of a biocompatible substance, including but not limited to normal saline, phosphate buffered saline, water, ethanol, DMSO, or electrolyte solutions (e.g., lactated ringers solution). Additionally, to assist in keeping the therapeutic compound at the target site, it may be administered attached to a targeting compound such as an antibody or protein, or it may be administered in a gel or semi-solid form associated with a polymer (e.g., pluronics, matrigel, polylysine, collagen), carbohydrate, lipid emulsion or other substance that would allow the therapeutic compound to stick to its target. Additionally the polymer could allow immediate release of the therapeutic compound or it could have controlled release properties.

Figure 1B:
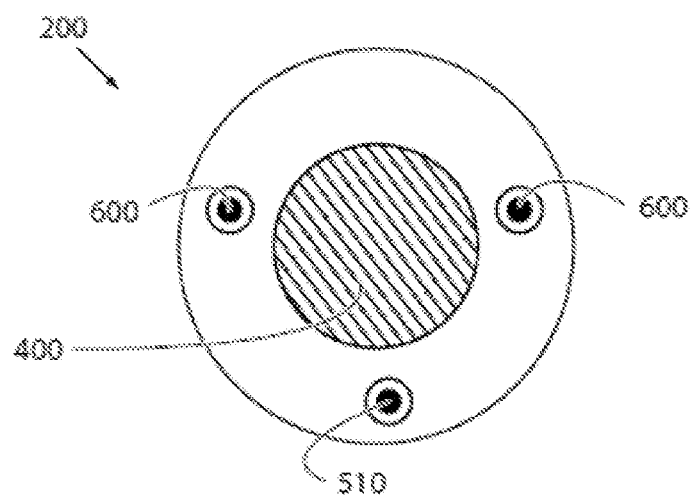
FIG. 1B is a cross-sectional view of the shaft of an embodiment if the device.
Figure 1C:
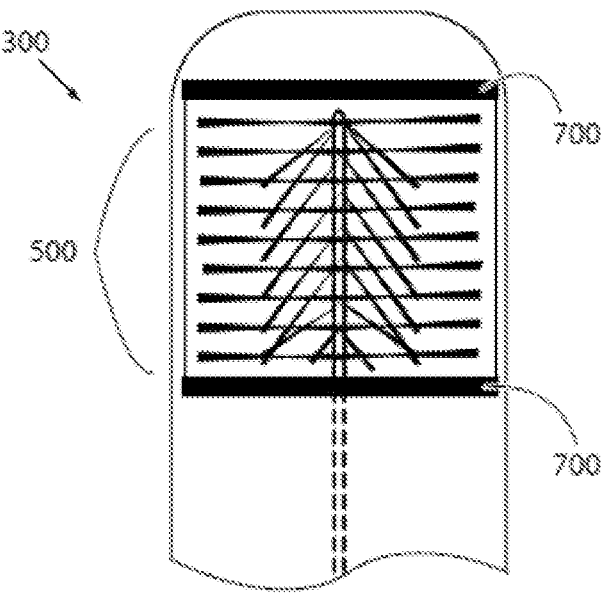
FIG. 1C is a transverse view of the tip portion of an embodiment of the device.

FIG. 1 depicts an embodiment of the device. A handle portion 100, a shaft portion 200 and a tip portion 300 may be seen in an exploded longitudinal view as illustrated in FIG. 1A. The handle portion 100 may include a steering drive 610 that for steering (e.g., a single wire for unidirectional steering or two wires for bidirectional steering), an operator interface, and a port for attachment of a syringe or other container that holds the therapeutic substance. The shaft portion 200 may include a fluid pathway channel (e.g., an inner lumen) through which a therapeutic substance may pass. The tip portion 300 may include an actuator 500 (e.g., a brush) that disperses the therapeutic substance. In an embodiment, the actuator 500 is a brush that may be connected to an actuator rod or cable 510 that traverses the device longitudinally. The brush can be manually manipulated or rotated or spun around by manipulation of the actuator rod or cable 510 where it exits the handle portion 100. FIG. 1B depicts a cross section of an embodiment where fluid pathway channel 400, steering lines 600, and actuator rod or cable 510 pass longitudinally through the device. FIG. 1C depicts an embodiment in which one or more radiographic marker 700 may be disposed in the tip portion 300 having actuator 500.

Figure 2A:
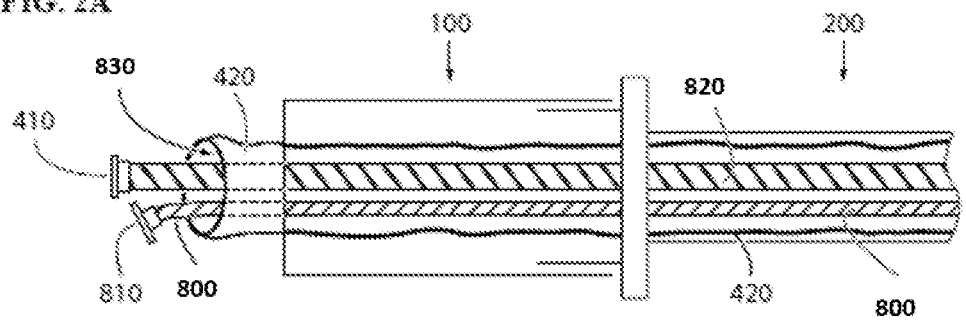
FIG. 2A is a transverse view of an embodiment of the device comprising a temperature control element.

In another embodiment, a temperature regulated chamber 810 may be provided as configured to keep the therapeutic substance within the fluid channel pathway 400 at the desired temperature. See FIG. 2A. Temperature control can be achieved by insulation of the shaft portion 200 and handle portion 100. Alternatively or in conjunction, temperature control can be achieved where the temperature regulated chamber 810, is an inner rod, for example, disposed within the fluid pathway channel 400, or a circumferential material 820 to the fluid pathway channel 400, or a circumferential chamber 830 to the fluid pathway channel 400 through which a temperature-controlling substance is circulated, any either of which may actively or passively control temperature of the material in the fluid pathway channel 400.

Figure 2B:
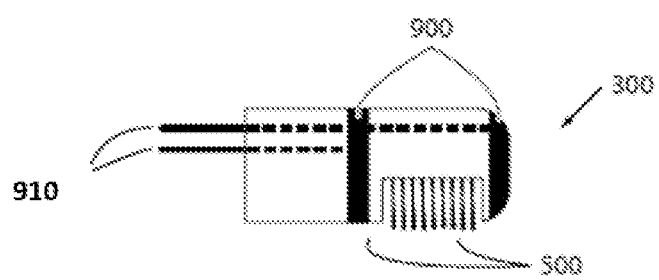
FIG. 2B is a transverse view of the tip portion of an embodiment of the device comprising a sensor.

In another embodiment, see FIG. 2B, one or more electrode 900 at the tip portion 300 may be provided. In such case, the electrode 900 may be operably connected by wire 910 to an electrogram recording system (such as Pruka, EPMedSystems, etc.) or wirelessly (e.g., Bluetooth™).

Figure 2C:
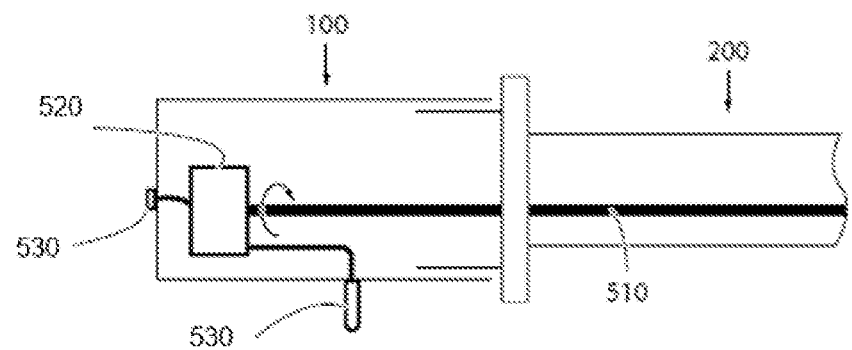
FIG. 2C is a transverse view of the handle portion of an embodiment of the device comprising actuator drive, power and control mechanisms.

In one other embodiment, see FIG. 2C; the actuator 500 and the actuator rod or cable 510 may be operably connected to a motor (such as a servomotor or other automated rotational system) in the handle portion or shaft portion that would be operably connected to a power supply (such as an electrical cord or portable battery supply). In the case of a brush as actuator 500, a connected servomotor could rotate the brush during delivery of the therapeutic. Control of the brush rotation speed could be achieved by an operator interface (such as a dial, knob or button) in the handle portion, whether or not brush control is manual or motorized. In other cases, the actuator 500 may be a foam tipped applicator head constructed of rayon, polyester, nylon or polyurethane. In some cases, the foam tipped applicator head may be reticulated 100 ppi Medical Grade foam thermally bonded to a rigid rectangular polypropylene shaft. In yet other cases, the actuator 500 may be a flocked swab applicator head constructed, for example, with Hydra-Flock® (Puritan Medical Products Co., LLC).

Figure 2D:
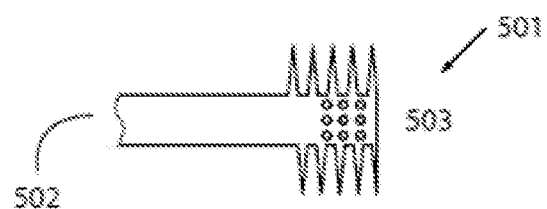
FIG. 2D is a transverse view of an embodiment of the device comprising an actuator with an internal lumen and a port.

In an embodiment, see FIG. 2D, the actuator 500 may have an actuator lumen 502 and an actuator lumen distal port 503. In some cases, these components may be a brush with holes either in the bristles or the bristle connection sites connecting to a hollow lumen rod that would allow delivery of the therapeutic substance through the brush rather than around the brush. In other cases, these components may be a foam tipped applicator head with holes connecting to a hollow lumen rod that would allow delivery of the therapeutic substance through the foam tipped applicator head rather than around the foam tipped applicator head.

Figure 2E:
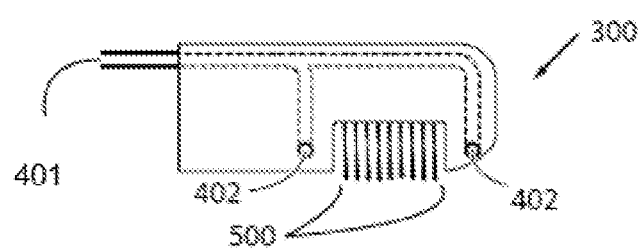
FIG. 2E is a transverse view of the tip portion of an embodiment of the device comprising an aspiration pathway.

In another embodiment, see FIG. 2E, a suction pathway channel 401 may be disposed within the fluid pathway channel. Here, suction pathway channel 401 may have one or more suction pathway channel distal port 402 in the tip portion 300 where suction pathway channel 401 is operably connected to a suction port in the handle portion 100. The suction pathway channel 401 could be used for removal of the therapeutic solution from around the tip portion 300 to further limit the spread of the infused therapeutic material beyond the intended cardiac delivery location.

As used herein, "fluid" refers primarily to liquids, but can also include suspensions of solids dispersed in liquids (dispersions, suspensions, colloidal mixtures), emulsions, liposomal compositions, and gasses dissolved in or otherwise present together within liquids inside the fluid-containing portions of syringes.

A "dosage form" or "formulation" refers to a drug or drug product which includes the active agent and may further include inactive substances such as excipients or diluents as are known in the art. The active agent may be a biologic, such as an antibody, protein, peptide or nucleic acid. A container used in conjunction with the drug delivery devices described herein, configured to deliver a selected dose, may include an additional volume of dosage form to account for "loss" in the delivery device.

References to "pharmaceutical agent," "pharmaceutically active," "pharmaceutical," "drug," "medicament," "active agent," "active drug" "active pharmaceutical ingredient," "API," and the like, refer in a general sense to substances useful in the medical and scientific arts as suitable for delivery via a syringe, including, for example, drugs, biologics, diagnostic agents (e.g., dyes or contrast agents) or other substances used for therapeutic, diagnostic, or preventative (e.g., vaccines), or research purposes. Example pharmaceutical agents include biologics, vaccines, chemotherapeutic agents, contrast agents, small molecules, immunogens, antigens, interferons, polyclonal antibody preparations, monoclonal antibodies, anesthetics, interfering RNAs, gene vectors, insulins, or combinations of any of these. As noted, a dosage form may comprise one or more active therapeutic agents, or a combination of active and diagnostic agents, etc.

"Inactive" substances refer to carriers, excipients, diluents, and the like, which are well-known in the art, although such substances may have beneficial function in the mixed injectable, such as, for example, surfactant, inorganic or organic salt, stabilizer, diluent, solubilizer, reducing agent, antioxidant, chelating agent, preservative, adjuvants, isotonic or buffering agents, or any excipient conventionally used in pharmaceutical compositions (i.e., "pharmaceutically acceptable excipient") and the like. These active or inactive substances may also include substances having immediate, delayed, controlled, or sustained release characteristics.

A "dosage form," "pharmaceutical formulation," "formulation," or "pharmaceutical composition" refers to a drug product that includes at least one active agent and may further include pharmaceutically acceptable excipients, carriers, buffers, stabilizers, or other materials well known to those skilled in the art. For example, a typical injectable pharmaceutical formulation includes a parenterally acceptable aqueous solution which is pyrogen-free and has suitable pH, isotonicity, and stability. The dosage forms delivered by the devices disclosed herein can have diagnostic, therapeutic, cosmetic, or research utility in various species, such as for example in human patients or subjects.

The term "therapeutic agent" as used herein refers to any therapeutically active substance that is administered to a subject to produce a desired, usually beneficial, effect. The term therapeutic agent includes, e.g., classical low molecular weight therapeutic agents commonly referred to as small molecule drugs; and biologics including, but not limited to, antibodies or functionally active portions thereof, peptides, lipids, protein drugs, protein conjugate drugs, fusion proteins, enzymes, nucleic acids, ribozymes, genetic material, viruses, bacteria, eukaryotic cells, and vaccines. A therapeutic agent can also be a pro-drug, which is metabolized into the desired therapeutically active substance at or after administration to a subject. In some aspects, the therapeutic agent is a prophylactic agent. In addition, the therapeutic agent can be pharmaceutically formulated. A therapeutic agent can also be a radioactive isotope. A therapeutic agent can be an agent activated by a form of energy such as light or ultrasonic energy, or activated by other circulating molecules that can be administered systemically or locally.

A pharmaceutical formulation can include a therapeutically effective amount of at least one active agent. Such effective amounts can be readily determined by one of ordinary skill in the art based, in part, on the effect of the administered dosage form, or the combinatorial effect of an agent and one or more additional active agents, if more than one agent is used. A therapeutically effective amount of an active agent can also vary according to factors such as the disease state, age, sex, and weight of the individual, and the ability of the agent (and one or more additional active agents) to elicit a desired response in the individual, e.g., amelioration of at least one condition parameter. For example, a therapeutically effective amount of a dosage form can inhibit (lessen the severity of or eliminate the occurrence of), prevent a particular disorder, or lessen any one of the symptoms of a particular disorder known in the art or described herein. A therapeutically effective amount may also be one in which any toxic or detrimental effects of the active agent or dosage form are outweighed by the therapeutically beneficial effects.

Accordingly, an active agent can be administered to a subject as a monotherapy. Alternatively, an active agent can be administered to a subject as a combination therapy with another active agent in a combination dosage form, or as an additional treatment, e.g., another treatment for an associated or additional disorder. For example, combination therapy can include administering to the subject (e.g., a human patient) one or more agents (e.g., antibiotics, anti-coagulants, anti-hypertensives, or anti-inflammatory drugs) that provide a therapeutic benefit to a subject. In some embodiments, an active agent and one or more additional active agents are administered in a single dosage form. In other embodiments, an active agent is administered first in time and an additional active agent(s) is administered second in time. In some embodiments, one or more additional active agents are administered at the same time, but using different drug delivery devices or delivery modes.

A dosage form delivered according to the devices described herein may replace or augment a previously or currently administered therapy. For example, upon treating with one pharmaceutical formulation, administration of an additional active agent(s) can cease or be diminished, e.g., be administered at lower concentrations or with longer intervals between administrations. In some embodiments, administration of a previous therapy can be maintained. In some embodiments, a previous therapy is maintained until the level of an active agent reaches a level sufficient to provide a therapeutic effect. Accordingly, two or more therapies can be administered in combination, sequentially, or simultaneously.

The term "antibody" includes a full antibody; a derivative, portion, or fragment thereof, such as a fragment derived from enzymatic or chemical cleavage or a portion obtained recombinantly; or a mimic of the binding region of an antibody produced either by way of protein expression techniques or through chemical synthesis, which retains functionality as a specific binding member, such as the specific binding activity of at least one antibody antigen-binding domain site. Accordingly, the term antibody includes monoclonal antibodies and all the various forms derived from antibodies, including but not limited to full-length antibodies (e.g., having an intact Fc region), bifunctional antibodies, trifunctional antibodies, antigen-binding fragments (e.g., produced via enzymatic cleavage) or portions (e.g., polypeptides produced using recombinant methods) including, for example, scFv, di-scFv, sdAb, BiTE (bi-specific T-cell engager), Fab, Fab' and F(ab')$_2$ fragments, diabodies, single chain antibodies, and other specific binding members comprising an antibody antigen-binding domain site. The terms "antibody" and "antibodies" as used herein also refer to human antibodies produced for example in transgenic animals or through phage display, as well as chimeric antibodies, humanized antibodies, and fully humanized antibodies or portions thereof that function as a specific binding member.

Biologics that can be advantageously delivered by the drug delivery devices as described herein include dosage forms comprising polymer solvent gels such as Eligard® (leuprolide acetate for injectable suspension); dosage forms comprising polymer solutions such as gelatin, hyaluronic acid (Hyalgan®), hylan GF 20 (Synvisc-One®), or a mixture of cyclodextrin and polymeric hyaluronate or polymeric hyaluronic acid (see U.S. Pat. No. 9,089,478) or cross-linked hyaluronic acid (U.S. Pat. No. 9,050,336); dosage forms comprising oily formulations, such as fulvestrant (Faslodex®); dosage forms comprising flowable polymer formulations, see WO2002030393 for example polymer microspheres, such as Lupron Depot® (leuprolide acetate for depot suspension); dosage forms comprising biologics, such as cells, platelets, cellular extracts, hormones, lubricin (proteoglycan), cytokines (e.g., granulocyte colony-stimulating factor), biomolecules having either agonist or antagonist activity (e.g., ligands or receptors), fusion proteins (such as a macromolecule having at least first and second functional moieties). References to a biologics include variants, analogs, or derivatives thereof, such as pegylated filgastrim.

Non-limiting examples of cardiac diseases that can be treated using the devices described herein include conduction system disease, sinus node dysfunction, atrial fibrillation, myocardial infarction, and heart failure. Other cardiac diseases may include rheumatic heart disease, hypertensive heart disease, ischemic heart disease, cerebrovascular disease, inflammatory heart disease, avalvular heart disease, aneurysm, atherosclerosis, peripheral arterial disease, angina, coronary heart disease, heart attack, stroke, transient ischemic attacks, cardiomyopathy, pericardial disease, valvular heart disease, congenital heart disease, cardiac arrhythmia, cardiomegaly, and heart neoplasia. Additional cardiac diseases may include acute decompensated heart failure, arteriosclerotic heart disease, athletic heart syndrome, atrioventricular fistula, autoimmune heart disease, Brown atrophy of the heart, Ebb Cade, cardiac amyloidosis, cardiac asthma, cardiac contractility modulation, cardiac syndrome X, cardiogenic shock, cardiophobia, cardiorenal syndrome, cardiotoxicity, carditis, coital angina, coronary artery aneurysm, coronary artery anomaly, coronary artery disease, coronary artery dissection, coronary artery ectasia, coronary occlusion, coronary steal, coronary thrombosis, coronary vasospasm, Coeur en sabot, Coxsackievirus-induced cardiomyopathy, diastolic heart failure, Dressler syndrome, Duroziez's disease, Eisenmenger's syndrome, embryocardia, embryonic recall, endocardial fibroelastosis, heart failure with preserved ejection fraction, high-output heart failure, hyperdynamic precordium, idiopathic giant-cell myocarditis, interventricular dyssynchrony, intraventricular dyssynchrony, isolated atrial amyloidosis, Keshan disease, Kounis syndrome, myocardial bridge, myocardial disarray, myocardial rupture, myocardial scarring, myocardial stunning, myocarditis, nonbacterial thrombotic endocarditis, Ostial disease, phosphorus and non-atherosclerotic heart disease, postpericardiotomy syndrome, pressure-controlled intermittent coronary sinus occlusion (PICSO), right axis deviation, Roemheld syndrome, Shone's syndrome, subacute bacterial endocarditis, traumatic cardiac arrest, ventricular aneurysm, and viral cardiomyopathy.

EXAMPLES

It should be understood that the examples and embodiments described herein are for illustrative purposes only and that various modifications or changes in light thereof will be suggested to persons skilled in the art and are to be included within the spirit and purview of this application and the scope of the appended claims. All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

(1) Treatment of conduction system disease by gene therapy. The catheter could be placed so that the tip portion 300 is in contact with the sinus node at the anterior aspect of the right atrium adjacent to where it connects with the superior vena cava. One or more electrode 900 in the catheter could target the sinus node by identifying the site of earliest electrical activation of the right atrium during sinus rhythm. The catheter could brush on the solution containing gene transfer vectors (adeno-associated virus, lentivirus, retrovirus, plasmids or other gene transfer vectors) encoding genes known to create automaticity in cardiac myocytes, fibroblast, or other cardiac cells.C Examples of these therapeutic genes include HCN1, HCN2, HCN3, HCN4, KCNJ2-AAA, TBX18, [adenylate cycylase, SCN4a, ADCY1) among others. In addition to delivery targeted specifically to the sinus node, the catheter could target any portion of the atria or ventricles where cardiac pacemaker activity might be desired.

(2) Treatment of sinus node dysfunction by cell therapy. The catheter could be positioned similarly to example 1. Instead of infusing gene transfer vectors, the catheter would brush on cells with pacemaker activity (either through endogenous function like induce pluripotent stem cells or embryonic stem cells directed to a pacemaker lineage, or through ex vivo modification of cells by gene therapy like gene transfer of the genes mentioned in example 1 into fibroblasts or mesenchymal stem cells). Cells could be delivered in saline or other liquid medium or in complex with matrigel, poloxamer or other agent to assist in cell retention.

(3) Treatment of conduction system disease by gene therapy. In patients with ventricular dyssynchrony, the catheter could be manipulated to deliver genes that would induce a Purkinje cell phenotype or an isolated, fast conducting channel (including but not limited to upregulation of GJA1, GJA5, NKX2.5, Tbx 5, Tbx 18, Gata 6, HCN4, KCNE1, KCNE2, SCN1a, SCN10a, SCN5a, Cav3.1, Cav1.3 or Kir3.1, or downregulation of Tbx3, RYR2, Cav1.2, or NCX1) in lines through, across or around the left ventricle to improve conduction and reduce the dyssynchrony.

(4) Treatment of conduction system disease by cell therapy. Modified cells that express a decremental conductance phenotype (e.g. induced pluripotent stem cells, cardiac stem cells, embryonic stem cells) could be brushed into the atrioventricular groove to electrically connect the atria to the ventricles. Additionally, either gene therapy as in example 3 or modified cells with a Purkinje phenotype could be brushed in lines through and across the left ventricle to reproduce the Purkinje system.

(5) Treatment of atrial fibrillation by gene therapy. Gene transfer vectors encoding genes shown to have antifibrillatory effect or structural remodeling preventive effect would be brushed on the atrial surface (either a subsection or all accessible atrial surfaces). Possible transgenes could include but are not limited to any or all of KCNH2-G628S (or other repolarization prolonging transgene), GJA1, GJA3, GJA5, CAMK2N2, or shRNA directed against CASP3, TGFβ, TNFα, KCNH2, KCHQ1. The gene transfer vector could be delivered in saline or other liquid medium or in complex with matrigel, poloxamer or other agent to assist in vector retention.

(6) Treatment of atrial fibrillation by pharmacotherapy. Antifibrillatory drugs (amiodarone, dofetilide, sotalol, flecainide, propafenone) complexed in retaining agents (pluronics, matrigel, polylysine, collagen, carbohydrate polymers) would be brushed on all exposed atrial surfaces or on strategic parts of the atria from which they could be distributed locally (e.g. delivery between the pulmonary veins in the posterior left atrium, or on the atrial free walls).

(7) Treatment of myocardial infarction by cell therapy. A myocardial infarction scar can be targeted by its MRI appearance or by echocardiographic guidance of the catheter or by use of the electrode option listed above to identify low voltage signals. Cardiac stem cells, induced pluripotent stem cells, mesenchymal stem cells or other useful cell type can be brushed onto the surface of the infarction with or without a matrix (matrigel, collagen, poloxamer) to retain the cells at the target. Cells can provide structural support, contractile support or paracrine functions to improve myocardial function or induce angiogenesis.

(8) Treatment of heart failure by gene therapy. The catheter can brush gene transfer vectors with or without a matrix for retention onto the ventricles. The gene transfer vectors would encode CaMK2N2, SERCA1, SERCA2a, angiogenesis genes (VEGF, FGF, PDGF), antiapoptotic genes (CASP3 inhibitory shRNA), antiinflammatory genes (TGFβ or TNFα inhibitory shRNA) or corrective genes for dilated or hypertrophic or arrhythmogenic cardiomyopathies, or other genes that have benefit for improvement of left ventricular function.

In an embodiment, the device could be packaged in a kit, which may include any or all of: a catheter to insert into anatomically distinct portions of the heart to define borders (as example, catheters could be inserted through the venous system and placed around the tricuspid valve annulus and through the coronary sinus to define the border between atria and ventricles); and/or steerable or nonsteerable sheath(s) through which the above mentioned brush catheter and the anatomical localization catheters would be inserted, contrast dye to further define anatomical structures by infusion into cardiac chambers, coronary arteries or veins, pulmonary arteries or veins. The cell solutions described herein, e.g., gene transfer vectors, infusion solutions, or complexing matrices could additionally be included in these kits. Accessory components of this embodiment (e.g., connecting power supplies for the servomotor or temperature control apparatus, electrode connection cables) could also be included in the kit.

The invention claimed is:

1. A method of treating a cardiac disease comprising delivering a therapeutic compound to a patient's heart using a device comprising a catheter, wherein the catheter comprises:
   a handle portion, a shaft portion, and a tip portion;
   a steering element configured to guide the catheter inside a patient's body;
   an internal conduit running along the longitudinal axis of the catheter;
   a fluid pathway disposed within the conduit; and
   a temperature control element configured to regulate the temperature of a fluid within the fluid pathway, wherein the temperature control element is an inner rod disposed within the fluid pathway;
   wherein the tip portion comprises an actuator configured to allow delivery of fluid through the actuator from the fluid pathway to the exterior of the catheter; and
   wherein the actuator is a foam tipped applicator head or a flocked swab applicator head with holes connecting to a hollow lumen rod.

2. The method of claim 1, wherein the therapeutic compound is selected from the group consisting of genetically engineered vectors, genetically engineered cells, proteins, stem cells, small molecule pharmaceuticals and biologics.

3. The method of claim 1, wherein the cardiac disease is selected from the group consisting of conduction system disease, cardiac arrhythmia, sinus node dysfunction, atrial fibrillation, myocardial infarction, and heart failure.

4. The method of claim 1, wherein the actuator is operably connected to a motor in the handle portion or shaft portion.

5. The method of claim 4, wherein the motor is configured to rotate the actuator during delivery of a therapeutic compound.

6. The method of claim 1, wherein the actuator is a foam tipped applicator head made of rayon, polyester, nylon or polyurethane.

7. The method of claim 1, wherein the actuator comprises an actuator lumen and an actuator lumen distal port.

8. The method of claim 1, wherein the actuator is a brush.

9. The method of claim 8, wherein the brush is configured to be manually manipulated or motor driven by manipulation of an actuator rod disposed in the handle portion.

* * * * *